(12) United States Patent
Amitai

(10) Patent No.: US 8,690,768 B2
(45) Date of Patent: Apr. 8, 2014

(54) PATIENT OPERABLE DATA COLLECTION SYSTEM

(76) Inventor: David Amitai, Ramat Gan (IL)

( * ) Notice: Subject to any disclaimer, the term of this patent is extended or adjusted under 35 U.S.C. 154(b) by 753 days.

(21) Appl. No.: 11/829,045

(22) Filed: Jul. 26, 2007

(65) Prior Publication Data

US 2009/0030286 A1 Jan. 29, 2009

(51) Int. Cl.
*A61B 5/00* (2006.01)
*G06F 19/00* (2011.01)

(52) U.S. Cl.
CPC .................................. *G06F 19/3406* (2013.01)
USPC ....................................................... 600/300

(58) Field of Classification Search
USPC ................ 600/300–301; 340/539.12–539.14; 705/2–5
See application file for complete search history.

(56) References Cited

U.S. PATENT DOCUMENTS

| | | | |
|---|---|---|---|
| 5,072,733 A * | 12/1991 | Spector et al. ................ | 600/439 |
| 6,282,440 B1 | 8/2001 | Brodnick et al. | |
| 6,396,416 B1 | 5/2002 | Kuusela et al. | |
| 6,478,736 B1 * | 11/2002 | Mault ............................ | 600/300 |
| 6,685,633 B2 | 2/2004 | Albert et al. | |
| 6,705,990 B1 * | 3/2004 | Gallant et al. ................ | 600/300 |
| 6,790,178 B1 * | 9/2004 | Mault et al. .................... | 600/300 |
| 6,873,869 B2 | 3/2005 | Fischer | |
| 6,952,912 B2 | 10/2005 | Lambert | |
| 6,974,419 B1 * | 12/2005 | Voss et al. ..................... | 600/485 |
| 7,038,588 B2 * | 5/2006 | Boone et al. ................ | 340/573.1 |
| 7,043,293 B1 | 5/2006 | Baura | |
| 7,052,467 B2 | 5/2006 | Johnson et al. | |
| 7,092,750 B2 | 8/2006 | VanEss | |
| 7,096,059 B2 | 8/2006 | Geddes | |
| 7,112,175 B2 | 9/2006 | Goppinathan et al. | |
| 7,115,102 B2 | 10/2006 | Abbruscato | |
| 7,244,230 B2 * | 7/2007 | Duggirala et al. ............ | 600/300 |
| 7,476,204 B2 * | 1/2009 | Parks et al. ................... | 600/593 |
| 7,946,994 B2 * | 5/2011 | Finburgh et al. .............. | 600/485 |
| 8,165,893 B1 * | 4/2012 | Goldberg et al. ................. | 705/2 |
| 8,224,663 B2 * | 7/2012 | Gordon .............................. | 705/2 |
| 2002/0032386 A1 * | 3/2002 | Sackner et al. ............... | 600/536 |
| 2002/0115912 A1 * | 8/2002 | Muraki et al. ................ | 600/300 |
| 2003/0069484 A1 * | 4/2003 | Blank et al. ................... | 600/310 |
| 2003/0220814 A1 * | 11/2003 | Gordon .............................. | 705/2 |
| 2004/0078219 A1 * | 4/2004 | Kaylor et al. ..................... | 705/2 |

(Continued)

FOREIGN PATENT DOCUMENTS

WO WO 2008/032234 3/2008

OTHER PUBLICATIONS

U.S. Appl. No. 60/820,780, filed Jul. 29, 2006, Berkner.

*Primary Examiner* — Bill Thomson
*Assistant Examiner* — Bobby Soriano
(74) *Attorney, Agent, or Firm* — Calvin B. Ward

(57) ABSTRACT

A portable interface device and a system utilizing the same are disclosed. A probe interface connects the interface device to a probe that collects data related to a physiological condition of a user in response to commands input to the interface device on the user interface. The data processor stores information specifying a position on a user's body at which a probe connected to the probe interface is to be positioned. The data processor displays a graphic on a display screen indicating a location on a user's body at which a probe connected to the probe interface is to be placed. A data processor records data from the probe when the probe is positioned as indicated in the graphic. The recorded data is communicated over the computer network to a server on the network.

9 Claims, 3 Drawing Sheets

(56) References Cited

U.S. PATENT DOCUMENTS

| | | | |
|---|---|---|---|
| 2004/0117215 A1* | 6/2004 | Marchosky | 705/3 |
| 2005/0049466 A1* | 3/2005 | Blank et al. | 600/310 |
| 2005/0065815 A1* | 3/2005 | Mazar et al. | 705/2 |
| 2005/0101841 A9* | 5/2005 | Kaylor et al. | 600/300 |
| 2005/0113703 A1 | 5/2005 | Farringdon et al. | |
| 2006/0030781 A1 | 2/2006 | Shennib | |
| 2006/0040245 A1* | 2/2006 | Airola et al. | 434/262 |
| 2006/0122525 A1 | 6/2006 | Shusterman | |
| 2006/0173269 A1* | 8/2006 | Glossop | 600/407 |
| 2006/0200029 A1* | 9/2006 | Evans et al. | 600/485 |
| 2006/0206358 A1* | 9/2006 | Beaver | 705/2 |
| 2006/0217620 A1 | 9/2006 | Bojovic et al. | |
| 2006/0224071 A1 | 10/2006 | Stewart | |
| 2006/0281975 A1* | 12/2006 | Yang | 600/300 |
| 2006/0293916 A1* | 12/2006 | Somberg | 705/2 |
| 2007/0056594 A1* | 3/2007 | El-Nokaly et al. | 128/897 |
| 2007/0123947 A1* | 5/2007 | Wenger et al. | 607/32 |
| 2007/0184422 A1* | 8/2007 | Takahashi | 434/262 |
| 2007/0192137 A1* | 8/2007 | Ombrellaro | 705/2 |
| 2007/0197887 A1* | 8/2007 | Lunak et al. | 600/323 |
| 2007/0239486 A1* | 10/2007 | Gordon | 705/2 |
| 2007/0241927 A1* | 10/2007 | Ratnakar | 340/825.28 |
| 2007/0274626 A1* | 11/2007 | Sabeta | 385/24 |
| 2008/0081967 A1* | 4/2008 | Andersohn et al. | 600/310 |
| 2008/0081982 A1* | 4/2008 | Simon et al. | 600/407 |
| 2008/0191864 A1* | 8/2008 | Wolfson | 340/524 |
| 2009/0305212 A1* | 12/2009 | McKenzie et al. | 434/266 |
| 2010/0019918 A1* | 1/2010 | Avital et al. | 340/686.4 |
| 2010/0222647 A1* | 9/2010 | Hashimshony et al. | 600/301 |

* cited by examiner

PATIENT OPERABLE DATA COLLECTION SYSTEM

BACKGROUND OF THE INVENTION

Traditional patient treatment models in which a patient with a potential problem goes to a medical facility (doctor's office, clinic, or hospital) for examination and treatment have several problems. First, the cost of delivering services in this manner is very high both in terms of monetary outlays and the patient's time. If the patient's complaint is relatively minor, or appears relatively minor to the patient, the patient is likely to forgo examination either because of the inconvenience and/or cost or because the patient cannot obtain a timely appointment with his or her physician. In the case of a patient who is a minor, the supervising parent may not be able to take the time off from work to bring the child to the child's doctor. Furthermore, even for patient's having health insurance, the economic costs are significant.

Second, the symptoms may disappear before the patient has a chance to be examined by his or her doctor. A patient with a heart condition may feel symptoms suggesting a cardiac event such as paroxysmal arrhythmias or, electrocardiographic changes detected during an angina pectoris event or chest pain episode. By the time the patient gets to a doctor and is hooked up to an ECG, the symptoms may have passed leaving the physician with uncertainty as to whether or not a significant heart event occurred.

Third, in many rural areas, a physician may not be available to treat the patient even if the patient can travel some distance to a clinic. Many countries or regions in countries have an acute shortage of medical personnel.

Finally, as the population ages in many of the developed countries, the need for a more efficient mechanism for delivering medical services and information is needed to reduce the economic costs of caring for the elderly. Even developed countries may find the cost of caring for the elderly under the traditional model to be too expensive.

Many systems that attempt to address all or part of these concerns by remote sensing of the patient's condition have been proposed. However, none of these proposed solutions have found widespread acceptance. For example, a number of systems that utilize remote ECG measurements to analyze a cardiac patient's condition have been proposed. These systems include some form of ECG electrodes that are attached to the patient's body and connected to a local processor carried by the patient. The local processor typically includes a transmitter that relays the measurements from the unit worn by the patient to a physician at a remote location. The relay mechanism can utilize a telephone line, either land or cellular, or some form of dedicated transmitter.

One problem with this type of system has to do with the placement of the electrodes on the patient's body. Correct placement of the electrodes is essential to providing useful data to the physician who must view the remotely acquired data. There are two types of systems in this regard. In the first, the electrodes are placed on the patient by the physician or a trained technician in the physician's office. In this case, the placement is ensured; however, the patient is restricted in his or her activities by the permanent placement of the electrodes. Simple tasks such as bathing and sleeping become problematic. Hence, this type of system is best suited for situations in which a cardiac event is expected over a relatively short period of time. In addition, the patient has the system in place for limited periods of time, and hence, the system may not be in place when an event occurs.

In the second type of system, the patient or a caretaker must place the electrodes on the patient's body when physical symptoms indicating that a cardiac event may be occurring are observed by the patient. This type of system relies on training the patient to correctly place the electrodes on his or her body. For many patients this is an unrealistic expectation. Furthermore, even a well-trained patient may have problems with the placement during a perceived cardiac event due to the physiological stress of the event.

While ECG measurements have been the subject of numerous patents, other forms of remote diagnostic instruments have been proposed. For example, systems that implement a stethoscope utilizing a microphone whose output is transmitted to a nurse or doctor who is at a remote location have also been suggested. Again, these systems rely on the correct placement of the microphone on the patient's body.

SUMMARY OF THE INVENTION

The present invention includes a portable interface device and a system utilizing the same. The interface device includes a display screen, a probe interface, a user interface, a data processing system, and a wireless network interface. The probe interface connects the interface device to a probe that collects data related to a physiological condition of a user in response to commands input to the interface device on the user interface. The data processor includes a memory for storing information specifying a position on a user's body at which a probe connected to the probe interface is to be positioned. The data processor displays a graphic on the display screen indicating a location on a user's body at which a probe connected to the probe interface is to be placed. The data processor records data from the probe when the probe is positioned as indicated in the graphic. The recorded data is communicated over the computer network to a server on the network. In addition, some processing of the data is carried out with the data processor in the interface device.

In one aspect of the invention, the data processing system in the interface device verifies the placement of the probe on the user's body. A camera in the interface device can be used for this purpose. In addition, comparison of the recorded data with exemplary data stored in the interface device can also be used to verify the probe placement.

In another aspect of the invention, the data processor compares readings taken with the probe with expected readings that are stored in the data processor and provides an indication to the user as to whether or not the compared readings are consistent with the expected readings.

In yet another aspect of the invention, the interface device includes a biometric sensor, the data processor identifying an authorized user of the apparatus by a biometric measurement made by the biometric sensor.

In a still further aspect of the present invention, the data processor stores data on a general medical condition associated with the user and the data processor displays that data in response to a logon protocol having been completed on the interface device.

An interface device according to the present invention is adapted for use in a system for recording and processing medical data. In one aspect of the invention, the system includes a plurality of portable interface devices as described above and a server connected to the portable interface devices by the Internet. The server includes a second data processor and memory for storing the recorded data from a plurality of such portable interface devices and a security interface for limiting access to the recorded data to a predetermined list of individuals or devices associated with each of the portable interface devices.

DETAILED DESCRIPTION OF THE PREFERRED EMBODIMENTS OF THE INVENTION

Figure 1:
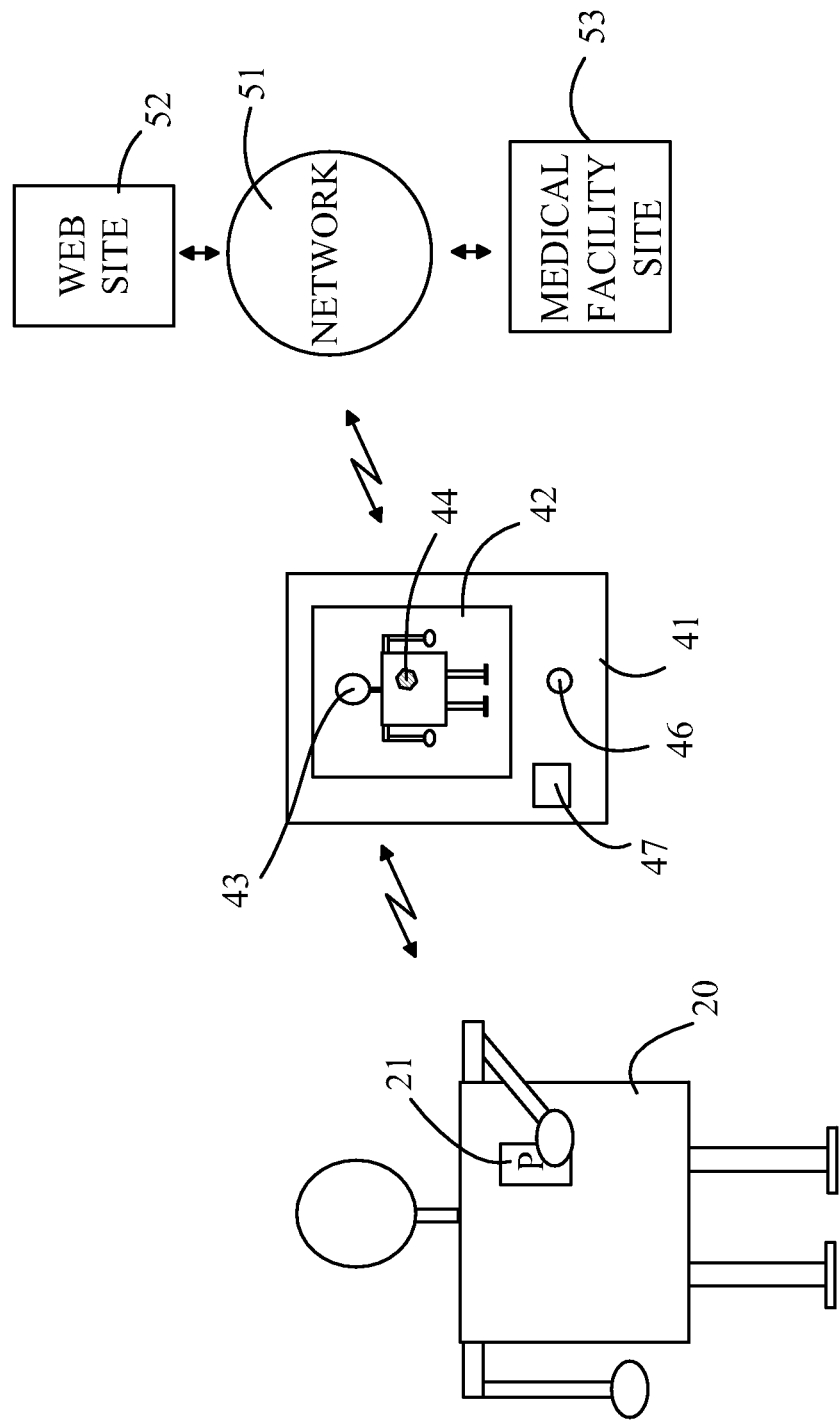
FIG. 1 illustrates a patient applying a probe to the patient's body and the transmission of the probe data for analysis and storage according to the present invention.

The manner in which the present invention provides its advantages can be more easily understood with reference to FIG. 1, which illustrates a patient applying a probe to the patient's body and the transmission of the probe data for analysis and storage according to the present invention. Patient 20 places a probe 21 on his body at a location specified by a local interface device 41. Interface device 41 includes a display screen 42 that displaces a diagram 43 showing the desired location 44 for the patient to place the probe. When probe 21 is properly placed, interface device 41 collects data from probe 21 and transmits that data via network 51 to a web site 52 that is accessible to medical personnel at medical facility 53. As will be explained in more detail below, in one embodiment of the present invention, interface device 41 has the ability to verify that probe 21 has been properly placed prior to the data being taken. Personnel and/or software at the medical facility can then review the data to determine the appropriate action, if any, which must be taken.

A probe according to the present invention can be any of a wide range of measurement devices, including an ECG probe for recording one or more traces of an ECG, a stethoscope, thermometer, or an optical imaging device that record images for transmission to the web site. In one embodiment of the present invention, the probes are separate from interface device 41 and communicate via a wireless link in the radio or optical ranges of the electromagnetic spectrum. WiFi and Bluetooth are two exemplary communication systems that are widely used for communication between devices. In addition, optical links in the infrared can also be utilized. It should also be noted that the probe and local interface device could communicate by acoustical means or be connected by wires.

A probe can also be implemented as part of interface device 41. For example, interface device 41 could include a microphone on the outer surface of the housing of the device that provides the functionality of a stethoscope. In this case, the user would place the housing against the user's body at the appropriate location so that the microphone could pickup the sounds for the particular test being implemented. In another example, the camera function could be implemented in interface device 41.

Local interface 41 can be implemented on any computational platform that can support communications between local interface 41 and a network, preferably the Internet. In one embodiment, local interface 41 is implemented on a handheld device such as a cellular telephone or PDA. In this case, the microphone and camera functions discussed above could be utilized by the handheld device for non-medical purposes such as talking on the telephone or taking a conventional picture. However, interface device 41 could be implemented on a laptop computer or even a desktop computer. In the simplest embodiment, local interface 41 stores the information needed to instruct the user on where to place a particular probe and communicates the probe data over network 51.

In one embodiment, local interface 41 includes an additional function that provides the user with feedback as to whether the probe is correctly placed. Consider an embodiment of the present invention in which interface device 41 includes a camera 46 and is positioned relative to the user such that the camera can observe the placement of probe 21 on the patient's body. Interface device 41 will have been previously programmed with a picture of the user with the probe correctly placed. Hence, interface device 41 need only include software to recognize the outline of the patient's body and the probe. To facilitate this recognition, probe 21 could include a distinctive color that is easily recognized.

In general, when a patient is provided with interface 41 and the probes to be utilized by the patient, the facility that is providing the system will show the patient how to use the probes and record the output of the probes at the correct locations and, optionally, at incorrect locations in the vicinity of the correct locations. If the probe's output differs significantly when placed at the incorrect locations in the vicinity of the correct locations, the differences can be used to direct the patient to move the probe to the correct location. Hence, the guidance can be provided even in the absence of a camera for probes whose outputs vary significantly with placement. For probes whose outputs do not vary significantly with placement, the need to provide precise placement is less critical.

In many cases, a patient wants to check that his or her condition has not changed significantly when the patient feels out of the ordinary. For example, a patient with a cardiac disease who feels pressure in the patient's chest needs to know if the pressure is the result of a cardiovascular event or some other non-related phenomenon such as indigestion. In this case, a measurement of one or more traces in an ECG followed by a comparison of the results with previously measured traces on that patient may be sufficient to rule out a new cardiac event.

Accordingly, in one embodiment of the present invention, interface device 41 includes a memory that stores information from previous measurements using one or more of the possible probes that could be utilized by the patient. The information could include an average of a number of prior measurements and a range of expected deviations from that average that would be considered to be normal for that patient. When the patient applies the probe and records the output, interface device 41 compares the measurement with the stored expected results and makes a determination as to whether the new measurements are within the expected range. If so, interface device 41 can provide that information directly to the patient, and hence, relieve the patient's anxiety. Interface device 41 could then send the measurements to server 52 that hosts a web site for storage and review on a non-critical basis.

In another embodiment of the present invention, interface device 41 includes software that allows interface 41 to determine if the patient would be at risk if the patient commenced some predetermined activity and warns the patient of the risk as a result of one or more measurements with a probe according to the present invention. For example, consider a patient with severe asthma who is about to take a trip in an airplane. Airplane cabins do not maintain sea level pressure. In general, the cabin is only pressurized to maintain a pressure of a few thousands of feet above sea level; hence, when a plane takes off from an airport at sea level and climbs to its cruising altitude, the patient will be subjected to a rapid change in altitude of several thousands of feet. If the patient's airways are badly constricted prior to boarding the plane, the change in altitude of the airplane cabin as the plane ascends could pose a significant health hazard to the patient. In this case, a stethoscope probe could be used to listen to the patient's lungs and determine if the lungs were constricted to the point where such a danger was present. In this case, the patient could take corrective action such as using an inhaler to medicate the patient's lungs prior to boarding the aircraft.

Figure 2:
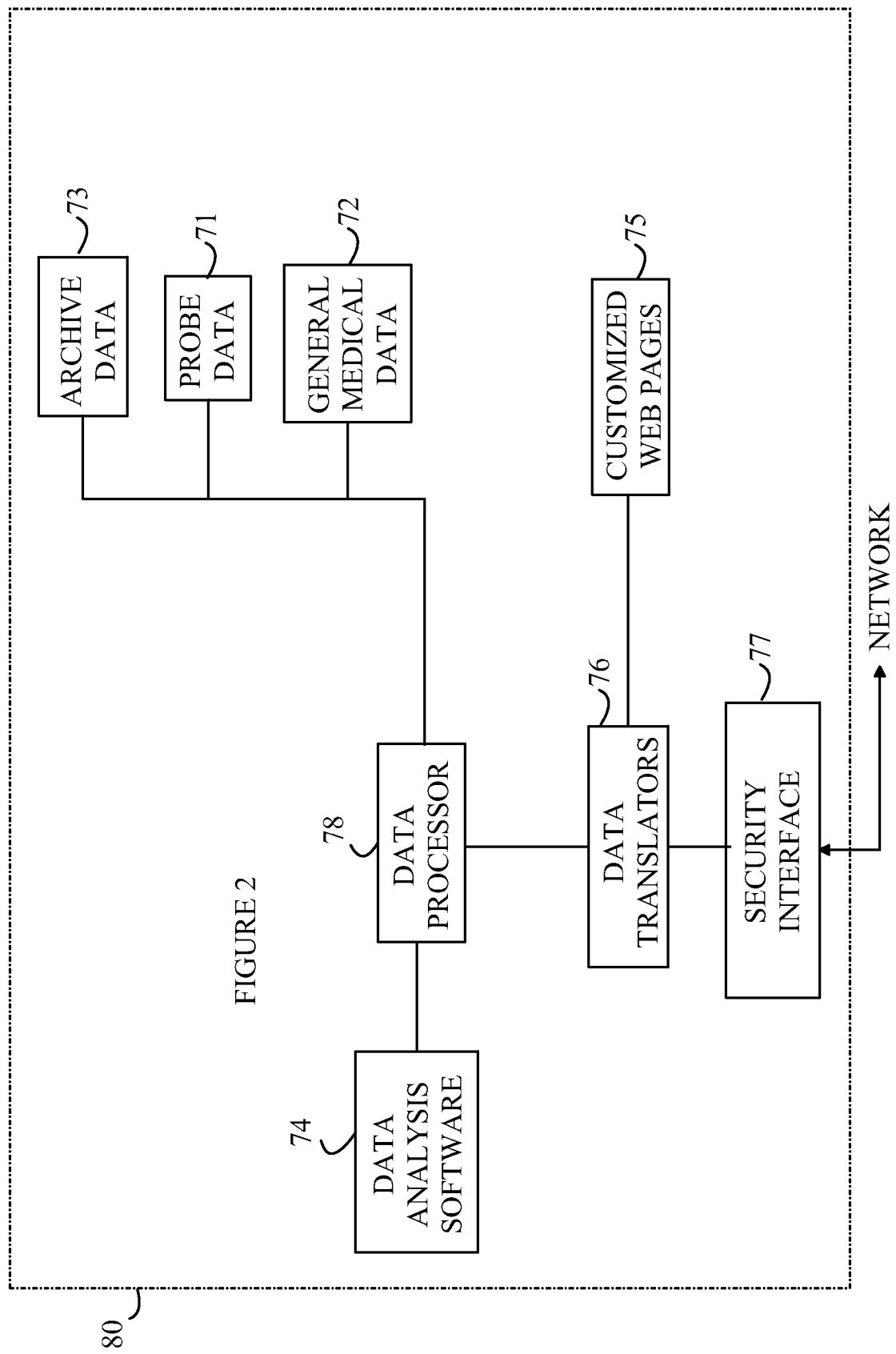
FIG. 2 illustrates one embodiment of a server according to the present invention.

In one embodiment of the present invention, interface 41 communicates with a server 52 over network 51. Server 52 provides a number of functions. Refer now to FIG. 2, which illustrates one embodiment of a server according to the present invention. Server 80 includes a data processor 78 that controls the various functions implemented on the server. Data flow into and out of server 80 is encrypted and requires an authorization code. Server 80 includes a security interface 77 that verifies the identity of the user and sets an access level for that user. The access level determines the type of data to which a user has access and the user's ability to change that data.

In addition, data processor 78 determines the type of interface that will be presented to the user for communicating data between the user and server 80. In one embodiment of the present invention, there is a customized web page 75 associated with each user. Data translators 76 are provided translating the data to the common format used to store information on server 80. For examples, patients communicating probe data to server 80 would be provided with a web page that is designed to receive data from the probes associated with that user. Physicians communicating with server 80 are presented with a web page that matches the pages that they are accustomed to seeing in their normal practice if that practice is computerized. Otherwise, a physician can chose from a plurality of generic web pages for viewing that patient's data. Physicians and/or medical facilities can also have a standardized web page for uploading and downloading data from the web site.

Server 80 acts as a storage site for data received from interface 41. The received data is initially stored in a probe data memory 71. Data from previous measurements is kept in a long-term archive 73. In addition, server 52 can provide storage for other medical data related to the owner of interface 41 in a general medical data memory 72. This data can include information on any medical conditions relevant to the owner. In addition, the data can include previously obtained data, both from interface 41 and other sources, such as the owner's personal physician or hospitals that treat the patient for one or more medical conditions.

Server 80 also stores data analysis software 74 that can be applied to data received from the patient. In general, this software is more complex and/or computationally intensive than the software that is normally run on interface 41. The software can be invoked in response to the patient uploading new probe data, in response to specific requests by the patient, or in response to a request by medical personnel having the appropriate level of access.

As noted above, patients are often treated by a plurality of medical groups, each with its own data storage system. In addition, a patient may change physicians from time to time because of a change in the patient's condition, preference in physicians, or a change in the patient's residence. Hence, medical personnel treating the patient in an emergency situation would be benefited by a single source that can access all of the patient's relevant data. Server 80 can provide a place for the patient to maintain his or her data that is independent of the particular medical organization currently attending to the patient. When the patient changes health care providers, the patient need only provide the appropriate level of access to the new provider. The new provider could then access the patient's past records and download copies onto that provider's computer system. When the new provider generates new data, the new provider can upload copies of the data to server 80 where that data can be available in medical emergencies.

The concentration of patient data in one location provides a security risk. Access by physicians and specific medical personnel can be secured through conventional data encryption and data certificates. However, emergency personnel do not necessarily have such authentication. Hence, providing access to the necessary data in an emergency while protecting the patient's data poses a challenge. In particular, the system must guard against a security breach if the interface device is lost or stolen while providing access in the case of an emergency in which the user is rendered unconscious.

In one embodiment of the present invention, server 80 will only make the data available to an individual who has not been previously cleared, after a key has been sent from interface 41, which is presumably with the patient at the time of the emergency. If the patient is unable to provide the transmission, an emergency key can be provided on interface 41. In one embodiment of the present invention, interface device 41 includes a biometric sensor 47. For example, biometric sensor 47 could be a fingerprint sensor. Even if the patient is unconscious, the emergency medical personnel could place the patient's finger on the sensor to obtain access to the patient's stored medical data. A combination of keys can also be utilized to restrict the data that is available. If the patient is unable to input a key in addition to the fingerprint image, the level of access would be set to provide only data that is useful to emergency medical personnel. Higher access could then be provided, if necessary, by an authorization from an individual listed in the emergency data through the web server.

In one embodiment of the present invention, the processing provided when the patient uploads new data is determined by a combination of the type of data, any requests made by the patient in the upload process, and predetermined instructions that are stored with the patient's medical data. For example, if the patient uploads a new ECG plot and requests a check as to whether the plot is normal or not, data processor 78 would invoke the appropriate data analysis software to compare the new plot with the previously stored plots and/or analyze the data using software that operates on the ECG plot without reference to the patient's previous ECG measurements. Data processor 78 could also execute a predefined program associated with the patient each time the patient uploads ECG data. That program could then provide information to the patient, as well as to the appropriate physician. If the data indicated an emergency situation, data processor 78 could also notify emergency personnel. In one embodiment of the present invention, interface device 41 includes a global positioning sensor that provides the location of interface device 41 so that the emergency personnel can be efficiently dispatched from the nearest location.

The above-described embodiments of the present invention assume that most of the patient's medical data and previous probe measurements are stored on a web server such as server 80 discussed above. However, copies of the more critical data could also be stored in interface device 41. In such embodiments, emergency medical personnel could access the critical data directly from interface device 41 without posing a security risk with respect to the remainder of the patient's data. In addition, such embodiments can provide the data when the patient is in a remote area that lacks Internet access.

Figure 3:
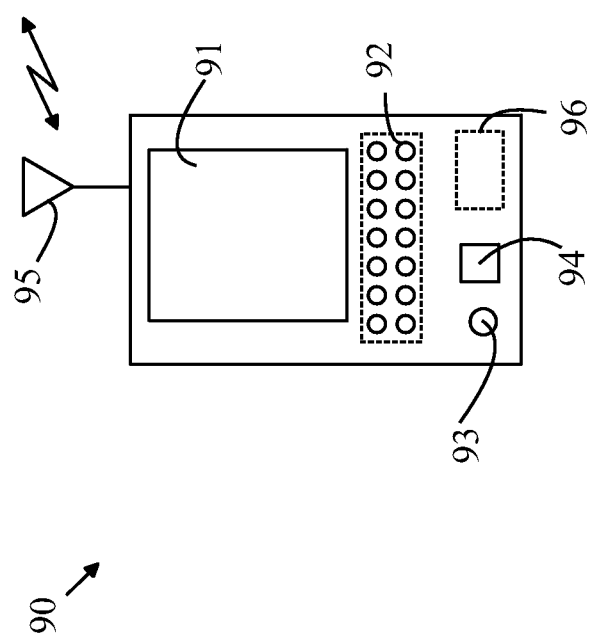
FIG. 3 illustrates one embodiment of an interface device according to the present invention.

An interface device according to the present invention can be constructed by appropriate modifications or extensions of a PDA or cellular telephone. Refer now to FIG. 3, which illustrates another embodiment of an interface device according to the present invention. Interface 90 is implemented on a PDA that includes a cellular telephone function and/or a WiFi communication link 95. The wireless communication link is also used to interface one or more probes to interface device 90. The probes are preferably interfaced using some form of limited range wireless link such as Bluetooth to prevent other probes in the vicinity of interface device 90 from interfering with the operation of the probe or probes that are sending data that is directed to interface device 90.

Interface device 90 includes a display screen 91 and a user input device such as a miniature keyboard 92. In addition, display screen 91 could be an interactive display screen in which the user inputs data by applying a stylus to the surface of display screen 91. As noted above, interface 90 can also include a camera 93. The camera can also act as a low-level biometric sensor for security purposes. In such applications, a picture is taken of the face of the user. If the picture matches a stored picture, access is granted. Alternatively, a more secure biometric sensor 94 can be included in interface device 91. The computational capacity of interface device 90 is provided by an embedded data processing system 96.

Various modifications to the present invention will become apparent to those skilled in the art from the foregoing description and accompanying drawings. Accordingly, the present invention is to be limited solely by the scope of the following claims.

What is claimed is:

1. An apparatus comprising:
a display screen;
a probe interface that connects said apparatus to a probe that collects data related to a physiological condition of a first user;
a user interface that receives commands from said first user of said apparatus;
a data processor comprising a memory that stores information specifying a position on a said first user's body at which a probe connected to said probe interface is to be positioned, said information including a picture of said first user with said probe positioned on said first user's body, wherein said data processor displays a graphic on said display screen indicating a location on said first user's body at which a probe connected to said probe interface is to be placed in response to a command being entered on said user interface by said first user, and wherein said data processor records data from said probe when said probe is positioned as indicated in said graphic;
a wireless network interface that connects said apparatus to a computer network, wherein said data processor communicates said recorded data over said computer network; and
a camera,
wherein said data processor compares a picture taken by said camera of said first user with said probe positioned on said first user's body with said stored picture of said first user with said probe positioned on said first user's body to determine if said probe is correctly positioned on said first user's body and communicates instructions to said first user on how to reposition said probe if said probe is not correctly positioned.

2. An apparatus comprising:
a display screen;
a probe interface that connects said apparatus to a probe that collects data related to a physiological condition of a first user;
a user interface that receives commands from said first user of said apparatus;
a data processor comprising a memory that stores information specifying a position on said first user's body at which a probe connected to said probe interface is to be positioned, wherein said data processor displays a graphic on said display screen indicating a location on said first user's body at which a probe connected to said probe interface is to be placed in response to a command being entered on said user interface by said first user, wherein said data processor records data from said probe when said probe is positioned as indicated in said graphic; and
a wireless network interface that connects said apparatus to a computer network, wherein said data processor communicates said recorded data over said computer network;
wherein said data processor stores a first set of exemplary readings from said probe when said probe is correctly positioned on said first user's body and wherein said data processor compares current readings from said probe with said first set to determine if said probe is correctly positioned on said first user's body and communicates instructions to said first user on how to reposition said probe if said probe is not correctly positioned.

3. The apparatus of claim 2 wherein said data processor stores a second set of exemplary readings from said probe when said probe is incorrectly positioned on said first user's body and wherein said data processor compares current readings from said probe with said second set in determining if said probe is correctly positioned.

4. An apparatus comprising:
a display screen;
a probe interface that connects said apparatus to a probe that collects data related to a physiological condition of a first user;
a user interface that receives commands from said first user of said apparatus;
a data processor comprising a memory that stores information specifying a position on said first user's body at which a probe connected to said probe interface is to be positioned, wherein said data processor displays a graphic on said display screen indicating a location on said first user's body at which a probe connected to said probe interface is to be placed in response to a command being entered on said user interface by said first user, wherein said data processor records data from said probe when said probe is positioned as indicated in said graphic; and
a wireless network interface that connects said apparatus to a computer network, wherein said data processor communicates said recorded data over said computer network,
wherein said data processor compares readings taken with said probe with expected readings that are stored in said data processor, and
wherein said data processor provides an indication to said first user as to whether or not said compared readings are consistent with said expected readings.

5. A system for recording and processing medical data, said system comprising:
a plurality of portable interface devices, each portable interface device comprising:
a display screen;

a probe interface that connects said portable interface device to a probe that collects data related to a physiological condition of a user;

a user interface that receives commands from said user of that portable interface device;

a first data processor comprising a memory that stores information specifying a position on said user's body at which a probe connected to said probe interface is to be positioned, wherein said first data processor displays a graphic on said display screen indicating a location on said user's body at which a probe connected to said probe interface is to be placed in response to a command being entered on said user interface by said user, wherein said first data processor records data from said probe when said probe is positioned as indicated in said graphic; and a wireless network interface that connects said apparatus to a computer network, wherein said first data processor communicates said recorded data over said computer network;

a server connected to said plurality of portable interface devices by the Internet, said server comprising:

a second data processor and memory that stores said recorded data from a plurality of such portable interface devices; and a security interface that limits access to said recorded data to a predetermined list of individuals or devices associated with each of said portable interface devices, said security interface requiring said user to be present at said corresponding portable interface device before access to said recorded data is allowed.

6. The system of claim 5 wherein an individual is associated with each of said portable interface devices and wherein said server also stores data related to a medical condition of one of said individuals, wherein said security interface provides access to said data related to said medical condition to individuals who have completed a logon procedure on said portable interface device associated with that individual.

7. The system of claim 6 wherein said logon procedure defines different levels of access to said stored data, wherein some portions of said stored data are not available at one of said levels of access but other portions of said stored data are available at said one of said levels of access.

8. The system of claim 5 wherein said server further comprises data analysis software and wherein said second data processor processes some of said recorded data with said data analysis software and returns a result to said portable interface device that sent said recorded data to said server.

9. The system of claim 8 wherein said server also sends said result to an individual other than said user associated with said portable interface device.

* * * * *